United States Patent [19]

Buckbinder et al.

[11] Patent Number: 5,840,673
[45] Date of Patent: Nov. 24, 1998

[54] INSULIN-LIKE GROWTH FACTOR BINDING PROTEIN 3 (IGF-BP3) IN TREATMENT OF P53-RELATED TUMORS

[75] Inventors: Leonard R. Buckbinder, Doylestown, Pa.; Nikolai Kley, Princeton Junction; Bernd R. Seizinger, Stockton, both of N.J.

[73] Assignee: Bristol-Myers Squibb Company, Princeton, N.J.

[21] Appl. No.: 713,052

[22] Filed: Sep. 12, 1996

Related U.S. Application Data

[60] Provisional application No. 60/003,730 Sep. 14, 1995.
[51] Int. Cl.$^6$ .............................. A61K 38/17; C12Q 1/02
[52] U.S. Cl. ............................... 514/2; 435/72; 435/69.1; 530/350; 530/399
[58] Field of Search ............................... 514/2; 435/69.1, 435/7.2; 530/350, 399

[56] References Cited

U.S. PATENT DOCUMENTS 5,573,925  11/1996  Halazonetis ............................. 435/69.7

FOREIGN PATENT DOCUMENTS

WO9404030  3/1994  WIPO .

OTHER PUBLICATIONS

Baserga et al., Adv. Exp. Med. Biol., vol. 343, pp. 105–112, 1994.
Buckbinder et al., Proc. Natl. Acad. Sci. USA, vol. 91, pp. 10640–10644, 1994.
Cohen et al., Molecular Endocrinology, vol. 7, No. 3, pp. 380–386, 1993.
Cubbage et al., J. Biol. Chem., vol. 265, No. 21, pp. 12642–12649, 1990.
Harrington, et al., The EMBO Journal, vol. 13, No. 14, pp. 3286–3295, 1994.
Baserga, Cell, vol. 79, pp. 927–930, 1994.
Pratt et al., Cancer Research, vol. 53, pp. 5193–5198, 1993.
Sell et al., Cancer Research, vol. 55, pp. 303–306, 1995.
El–Deiry et al., Cell, vol. 75, pp. 817–825, 1993.
Goldring et al., Eukar. Gene Express, vol. 1, pp. 301–321, 1991.
Oh et al., Growth Reg., vol. 3, pp. 113–123, 1993.
Hermeking et al., Science, vol. 265, pp. 2091–2093, 1994.
Moerman et al., Exp. Geronotol., vol. 28, pp. 361–370, 1993.
Grigoriev et al., J. Cell. Physiol., vol. 160, pp. 203–211, 1994.
Buckbinder et al., Nature, vol. 377, pp. 646–649, 1995.
Oh et al., Progress in Growth Factor Research, vol. 6, No. 2–4, pp. 503–512, 1995.
Bertherat, Eur. J. Endocrinol., vol. 134, No. 4 pp. 426–427, 1996.
Ludwig et al., Molecular and Cellular Biology, vol. 16, No. 9, pp. 4952–4960.

*Primary Examiner*—Sally P. Teng
*Attorney, Agent, or Firm*—Timothy J. Gaul

[57] ABSTRACT

Methods of treating p53-related tumors by administering (1) a modulator of IGF-BP3, wherein the modulator upregulates IGF-BP3 expression or activity, (2) IGF-BP3 itself, or (3) an expression vector comprising a nucleotide sequence encoding IGF-BP3. In the latter method, the IGF-BP3 nucleotide sequence may also be operatively linked to an inducible promoter or enhancer, wherein the method further comprises administering an inducer capable of initiating or upregulating expression of the protein. Furthermore, any of the foregoing methods may include as an additional step administration of a cytotoxic agent. These methods are specific examples of a broader method: treatment of p53-related tumors by inhibiting the binding of IGF to IGFR.

4 Claims, 14 Drawing Sheets

37° 30°

IGF-BP3

GAPDH 1  2

BOX A (nts 3158-3178)

```
AAACAAGCCACCAACATGCTT
:::|::|::  ::|:::|:::
RRRCWWGYYYNRRRCWWGYYY
```

BOX B (nts 4078-4097)

```
GGGCAAGACCTGCCAAGCCT
:::|::| ::  :  |:::|:::
RRRCWWGYYYRRRCWWGYYY
```

FIG. 2a

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 358 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:1:

```
CCCAGGATGG  CTTTTGCTGC  GGCCCCGTGG  GGTAGGAGGG  ACAGAGAGAC  GGGAGAGTCA       60
GCCTCCACAT  TCAGAGGCAT  CACAAGTAAT  GGCACAATTC  TTCGGATGAC  TGCAGAAAAT      120
AGTGTTTTGT  AGTTCAACAA  CTCAAGACGA  AGCTTATTTC  TGAGGATAAG  CTCTTTAAAG      180
GCAAAGCTTT  ATTTTCATCT  CTCATCTTTT  GTCCTCCTTA  GCACAATGTA  AAAAAGAATA      240
GTAATATCAG  AACAGGAAGG  AGGAATGGCT  TGCTGGGGAG  CCCATCCAGG  ACACTGGGAG      300
CACATAGAGA  TTCACCCATG  TTTGTTGAAC  TTAGAGTCAT  TCTCATGCTT  TTCTTTAT       358
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
AAACAAGCCA  CCAACATGCT  T                                                   21
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GGGCAAGACC  TGCCAAGCTT                                                      20
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

```
RRRCWWGYYY NRRRCWWGYY Y                                              21
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "CONSENSUS COMPETITOR IN DNA
            BINDING REACTIONS AND EMSA ANALYSIS"

(xi) SEQUENCE DESCRIPTION: SEQ ID NO:5:

```
GATCTACCCA GGCTTGGCAG GTCTTGCCCT CCTC                                34
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "MUTANT COMPETITOR IN DNA
            BINDING REACTIONS AND EMSA ANALYSIS"

(xi) SEQUENCE DESCRIPTION: SEQ ID NO:6:

```
TCGAGCTTTG GACTTTTCT GGCCA                                           25
```

INSULIN-LIKE GROWTH FACTOR BINDING PROTEIN 3 (IGF-BP3) IN TREATMENT OF P53-RELATED TUMORS

CROSS-REFERENCE TO RELATED APPLICATION

This application claims the benefit of U.S. provisional application No. 60/003,730 filed Sep. 14, 1995.

FIELD OF THE INVENTION

The present invention relates to methods of using a protein designated IGF-BP3, which affects apoptosis and tumor suppression. This invention also relates to methods of identifying and using modulators and mimetics of IGF-BP3.

BACKGROUND OF THE INVENTION p53 is a tumor suppressor well known in the art. Upregulation and activation of p53 are an important cellular response to genotoxic stress and deregulated expression of certain oncogenes. Hartwell et al. (1994), *Science* 266: 1821–8. Accordingly, p53 is required for cell cycle arrest at the G1 checkpoint. Hartwell et al. (1994); Kuerbitz et al. (1992), *Proc. Natl. Acad. Sci USA* 89: 7491–5; Kastan et al. (1991), *Cancer Research* 51: 6304–11. Alternatively, p53 in many instances is required as a link to apoptosis in response to certain anticancer agents and γ-irradiation. Yonish-Rouach et al. (1991), Nature 352: 345–7; Shaw et al. (1992), *Proc. Natl. Acad. Sci USA* 89: 4495–9; Lowe et al. (1993), *Nature* 362: 847–9; Clark et al. (1993), *Nature* 362: 849–52; Lowe et al. (1994), *Cell* 74: 957–67. p53 might also be required as a link to apoptosis in response to E1A and c-myc oncoprotein expression. Debbas et al. (1993), *Genes & Development* 7: 546–54; Lowe et al. (1993), *Genes & Development* 7: 535–45; Evan et al. (1992), *Cell* 69:119–28; Hermeking & Eick (1994), *Science* 265: 2091–3.

The tumor suppressor function of p53 is thought to be mediated, at least in part, by its ability to act as a sequence-specific transcriptional activator. Genes such as p21/WAF1 (El-Deiry et al. (1993), *Cell* 75: 817–25) and GADD45 (Kastan et al. (1992), *Cell* 71: 587–97) are p53-regulated target genes. These genes encode proteins that directly interact with components of the cell cycle and DNA replication machinery and provide a direct link between the p53-dependent G1 checkpoint in the cell cycle, DNA repair and cellular proliferation. Harper et al. (1993), *Cell* 75:805–16; Xiong, et al. (1993), *Nature* 366:701–4; Smith et al. (1994), *Science* 266:1376–80.

The insulin-like growth factors (IGF-I and -II), together with their receptors (IGFR), promote tumor cell growth. IGF-I (and to some extent IGF-II) is a mitogen that stimulates cellular proliferation (associated with elevated cyclin D1 and cdc2) and transformation. More recently, studies suggest that IGF-I acts as a survival factor, protecting cells from undergoing apoptosis (cell death). Sell, C. et al. (1995), *Cancer Research* 55: 303–6. This latter activity may be particularly important in promoting tumor cell growth. Animal studies clearly suggest a role for IGF-I and IGF-IR in tumor growth.

The insulin-like growth factor binding protein-3 (IGF-BP3) regulates the IGF-IGFR axis. Cubbage and colleagues recently described 8.9 kb of genomic sequence, including the promoter and 1.9 kb of 5' flanking sequence, five exons, four introns and approximately 1.5 kb of 3' flanking sequence for the IGF-BP3 gene. Cubbage et al. (1990), *J. Biol. Chem.* 265: 12642–9. We incorporate this publication by reference, including the sequence of IGF-BP3.

The art describes use of IGF-BP3 in combination with IGF for treatment of catabolic conditions (e.g., burns, trauma, peptic ulcers). International Patent Application WO 9404030. The art does not describe, however, any link between the IGF-binding activity of IGF-BP3 and the tumor suppressor p53.

SUMMARY OF THE INVENTION

The present invention concerns methods of treating p53-related tumors. The term "p53-related" refers to tumor cells in which wild-type (wt) p53 is absent, disabled or otherwise mutated. These methods of treatment comprise administering an effective amount of either (1) a modulator of IGF-BP3, (2) IGF-BP3 itself, or (3) an expression vector comprising a nucleotide sequence encoding IGF-BP3. In method (1), the modulator upregulates IGF-BP3 expression or activity. In method (3), one may also operatively link the IGF-BP3 nucleotide sequence to an inducible promoter or enhancer, and the method further comprises administering an inducer capable of initiating or upregulating expression of the protein. Furthermore, any of the foregoing methods may include as an additional step administration of a cytotoxic agent, as the present inventors believe that IGF-BP3 can make tumor cells more susceptible to such agents.

The foregoing methods inhibit binding of IGFs to IGFR. Thus, these methods are specific examples of a broader method: treatment of p53-related tumors by inhibiting the binding of IGF to IGFR.

The invention further concerns methods of identifying substances useful in treatment of p53-related tumors. One such method uses a reporter gene operatively linked to the p53-responsive elements described below, wherein expression of the reporter signals upregulation of IGF-BP3. Another such method employs a cancer cell having IGF-I or -II receptors in the presence of bases or nucleotides having a detectable label, wherein a decrease in uptake of the label signals a decrease in IGF-directed DNA synthesis.

DESCRIPTION OF THE DRAWINGS

FIG. 1a shows the genomic structure of the IGF-BP3 gene indicating the map location (nucleotides 8095–8452) and nucleotide sequence (SEQ. ID. NO.: 1) of the cDNA fragment, probe V9. FIG. 1b shows a comparative northern blot analysis of p53-induced IGF-BP3 mRNA expression in $CdCl_2$-activated EB-1 cells. In FIG. 1c, a temperature-sensitive mutant of p53 (p53V143A) induces expression of IGF-BP3 mRNA in the clonal Saos-2-D4H cells described in Buckbinder et al. (1994), *Proc. Natl. Acad. Sci. USA* 91: 10640–4. FIG. 1d shows kinetic analysis of p53-regulated transcript expression in $CdCl_2$-activated EB-1 cells. We monitored expression by northern blot analysis, normalized to actin expression, and quantitated expression by phosphoimaging analysis (Fuji phosphoimager).

FIG. 2 shows characterization of p53-binding and p53-responsive DNA elements in the IGF-BP3 gene. FIG. 2a shows two sequences (SEQ. ID. NOS.: 2 and 3) in the published IGF-BP3 gene structure that we determined by computer analysis to have similarity to the p53 consensus binding site $(RRRCWWGYYY)_2$ (SEQ. ID. NO.: 4). These sequences are denoted here Box A (SEQ. ID. NO.: 2) and Box B (SEQ. ID. NO.: 3) and appear in the first and second introns, respectively.

DETAILED DESCRIPTION OF THE INVENTION

We describe herein a novel mechanism whereby p53 regulates tumor growth. Specifically, we have discovered that (1) p53-responsive DNA elements reside in the first and second introns of the IGF-BP3 gene; (2) wild type but not mutant p53 induces the IGF-bp3 gene; and (3) this response is associated with an increase in both synthesis and secretion of IGF-BP3 into the extracellular space.

Figure 4A:
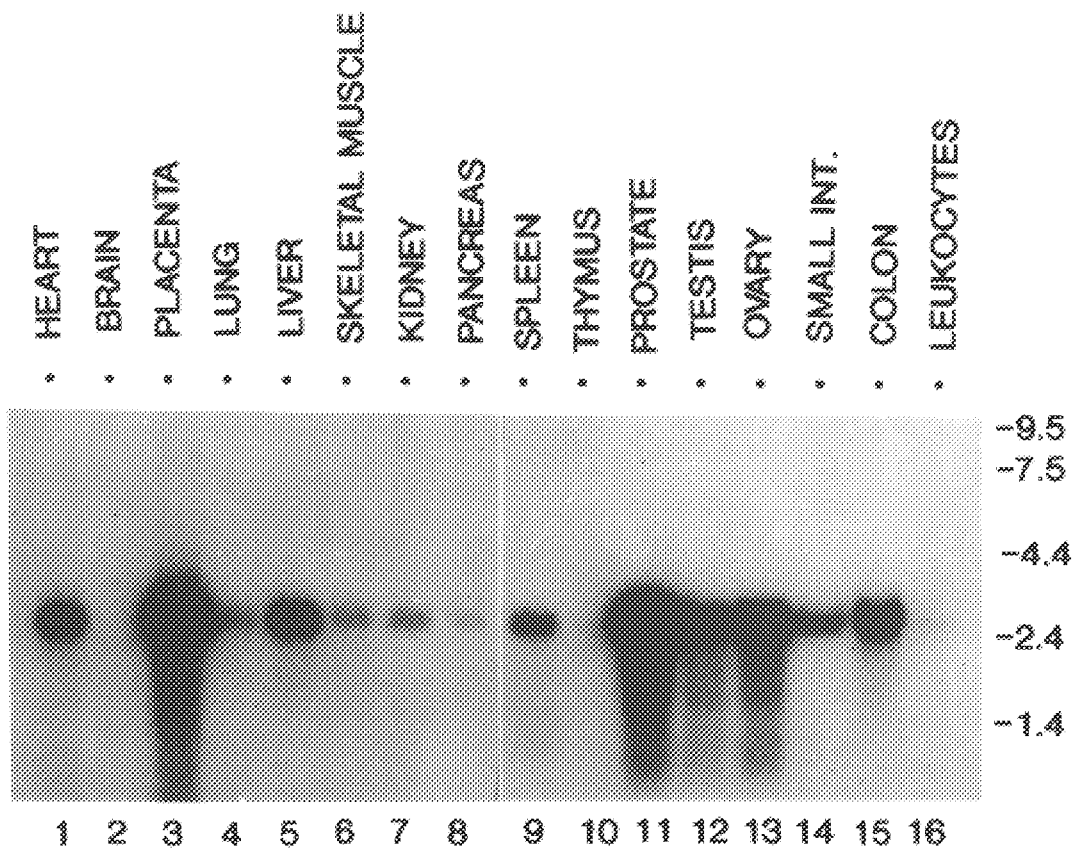
FIG. 4a shows expression of IGF-BP3 mRNA in human tissues.
Figure 4B:
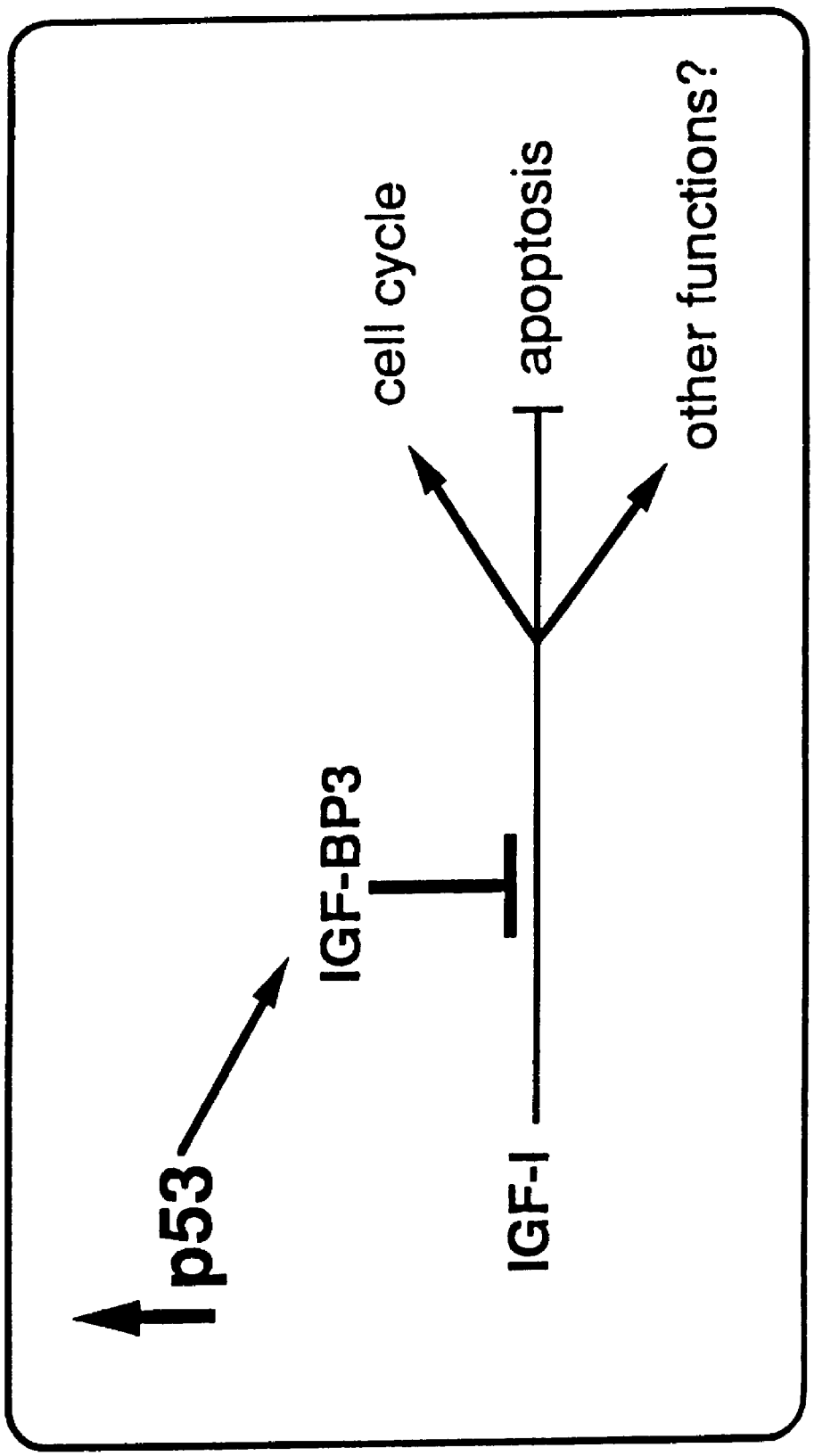
FIG. 4b shows a working model linking p53 to IGF-regulated signaling pathways.
Figure 5A:
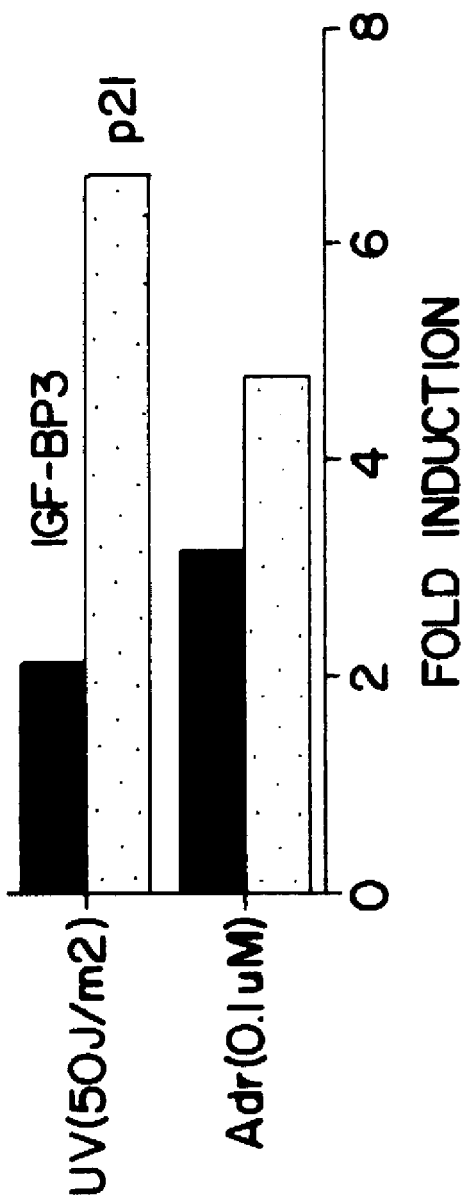
FIG. 5a shows induction of IGF-BP3 by DNA damaging agents.
Figure 5B:
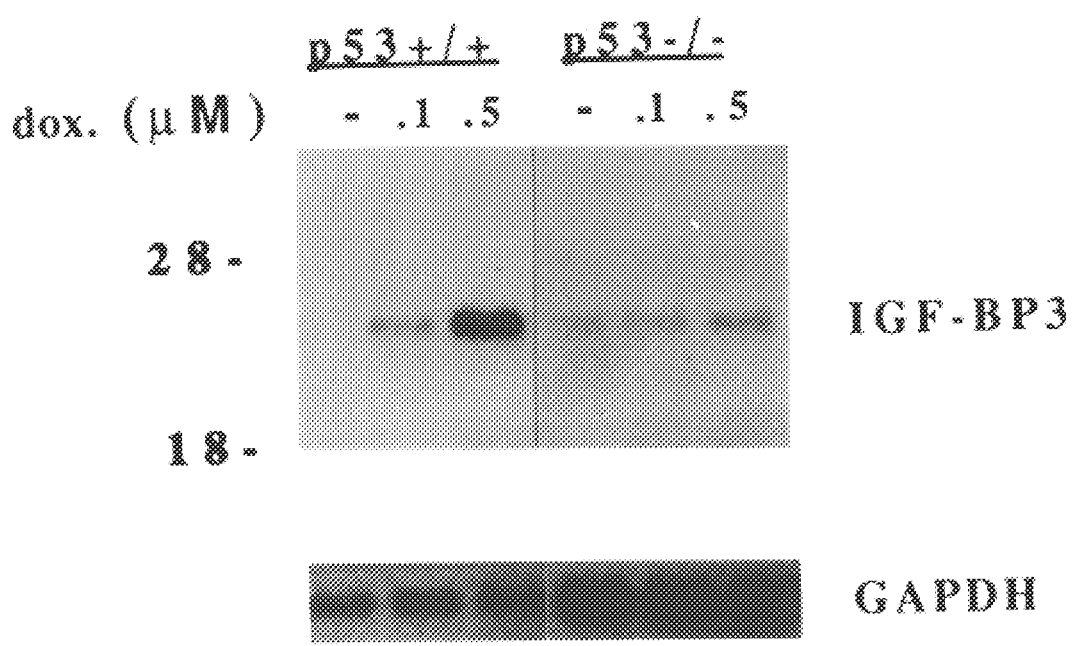
FIG. 5b shows that induction of IGF-BP3 by DNA damaging agents is dependent on p53.

Our discovery links p53 to the autocrine/paracrine IGF-I (and II) cytokine/IGF-receptor (IGFR) axis (See FIG. 4b). IGF-BP3 binds IGFs and prevents interaction with their IGFRs, thus acting as a growth inhibitor. Furthermore, IGF-BP3 may have growth-inhibitory effects not related to its ability to interact with the IGFs, but rather mediated by an IGFR-independent signaling pathway. Thus, IGF-BP3 may be linked to two distinct signaling pathways associated with cellular growth inhibition.

The present discovery suggests that one can treat human tumors, in particular those with p53 mutations, by increasing or mimicking IGF-BP3 functions. This method can employ modulators of IGF-BP3, which one can identify by methods described herein. Such modulators upregulate IGF-BP3 expression or activity. One type of such modulators binds to one or both of IGF-BP3's p53-responsive elements (Boxes A and B; SEQ. ID. NOS.: 2 and 3, respectively).

Another method employs IGF-BP3 protein itself. In this method, one administers IGF-BP3 protein or recombinant protein (e.g., as supplied by UBI). For this method, one produces, purifies, and formulates the protein for administration by methods known in the art (e.g. Tressel, T. J. et al. (1991), *Biochem. Biophys. Res. Commun.* 178: 625–33).

Still another method of treatment employs an expression vector comprising a nucleotide sequence encoding IGF-BP3. Suitable expression vectors include plasmids, but this invention includes other forms of expression vectors that now exist or become known in the art subsequently hereto. In addition, a useful expression vector typically contains an origin of replication, a promoter upstream from the coding sequence a transcription termination sequence. The expression vector may also include other DNA sequences known in the art, such as: stability leader sequences, which stabilize the expression product; secretory leader sequences, which enable secretion of the expression product; environmental feedback sequences, which enable modulation of expression (e.g., by the presence or absence of nutrients or other inducers in the growth medium; marker sequences, which enable phenotypic selection in transformed host cells; restriction sites, which enable cleavage by restriction endonucleases; and sequences that enable expression in various types of hosts, including prokaryotes, yeasts, fungi, plants and higher eukaryotes.

The cloning/expression vector directs the replication and expression, of the nucleic acids of the present invention. Suitable origins of replication include, for example, the Col E1, the SV40 viral and the M13 origins of replication. Suitable promoters include, for example, the cytomegalovirus promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like. All of these materials are known in the art and are commercially available.

Persons skilled in the art can construct vectors having the foregoing features by recombinant DNA techniques known in the art. See Sambrook et al., *Molecular Cloning: A Laboratory Manual*, Second Edition, Cold Spring Harbor Laboratory, Cold Spring Harbor, N.Y. (1989). Alternatively, they can use commercially available vectors that already incorporate these features. Suitable commercially available vectors include the baculovirus expression vector pBlueBac, the prokaryotic expression vector pcDNAII and the yeast expression vector pYes2 (Invitrogen Corp., San Diego, Calif.).

In this method, the IGF-BP3 sequence may be under the control of a constitutive or inducible promoter. In the latter instance, one co-administers an inducer. Suitable inducible promoters include mouse mammary tumor virus promoter and dexamethasone, metallothionein promoter and zinc, yeast gal 4 promoter and galactose and the like.

In addition, since IGF-I plays a role in apoptosis, inhibition of the IGF-I-IGF-IR axis could sensitize tumor cells to conventional cytotoxic agents or radiation and provide a novel therapeutic approach to cancer treatment. Thus, one can co-administer a cytotoxic agent or other anti-cancer agent as an additional step in the foregoing methods. Suitable cytotoxic agents include paclitaxel, cisplatin, etoposide, paraplatin, bleomycin, plicamycin, doxorubicin, dimethyl triazeno imidazole carboxamide (DTIC), daunorubicin, cytarabine, procarbazine, 1-($\beta$-chloroethyl)-1-nitrosourea (CCNU), hydroxyurea, melphalan, 1,3-bis ($\beta$-chloroethyl)-1-nitrosourea (BCNU), vincristine, vinblastine, o,p'-dichloro-diphenyldichloroethane (o,p'-DDD) (mitotane), cyclophosphamide, ifosfamide (a cyclophosphamide derivative), 5-fluorouracil, busulfan, dactinomycin, mitomycin-C, 6-thioguanine, thio-TEPA, chloroambucil, 6-mercaptopurine, methotrexate, nitrogen mustard, and the like. Other suitable anti-cancer agents include interferon, tamoxifen, testolactone, L-asparaginase, progesterone (megace, megestrol acetate), prednisone, androgens, estrogens, and the like. One could administer the foregoing agents in about the dosage and mode known in the art. Other suitable cytotoxics and other anti-cancer agents are listed in the Food and Drug Administration's "Orange Book," i.e., Approved Drug Products with Therapeutic Equivalence Evaluations, U.S. Dept. of Health and Human Services (1994), and its 1995 supplements.

The invention further concerns methods of identifying substances useful in treatment of p53-related tumors. One such method involves introducing into a host cell (e.g., by transfection) a construct having either or both of Box A and Box B (SEQ. ID. NOS.: 2 and 3) operatively linked to a reporter gene. As used in this context, the term "operatively linked" means that the regulatory DNA sequences (SEQ. ID. NOS.: 2 and 3) are capable of increasing the expression of the RNA encoded by the reporter gene. The regulatory sequences may be upstream of the coding region, downstream, or in an intron as in the gene for IGF-BP3. The reporter gene may be any number of reporters known in the art, such as luciferase, lacZ, chloramphenicol transferase (CAT), and the like.

After introducing the construct into the host cell, one can then treat the host cell with test substances. A test substance that binds to SEQ. ID. NO.: 2 or 3 will upregulate expression of the reporter gene. This method identifies such a substance as an IGF-BP3 modulator that can treat p53-related tumors.

Another method of identifying substances useful in treating p53-related tumors exploits our observation that p53-induced IGF-BP3 acts by inhibiting IGF-induced DNA synthesis (FIG. 3). This method employs DNA bases (adenosine, thymidine, cytosine, or guanidine) or nucleotides (ATP, GTP, TTP, or CTP) having a detectable label. Suitable detectable labels include tritium-labeled thymidine (see FIG. 3 and Materials and Methods), 5'-bromo-2'-deoxyuridine and the like. In this method, one treats a cell with the labeled compound, a test substance, and IGF-I or IGF-II. For purposes of this method, "IGF-I" and "IGF-II" include recombinant variants thereof such as those supplied by UBI. One monitors IGF-I-dependent DNA synthesis by the cell's uptake of the label in the presence of varying concentrations of IGF and the test substance, as shown in FIG. 3. If a test substance decreases IGF-dependent DNA synthesis, then it is useful in treating p53-related tumors.

Another method identifies compounds that mimic IGF-BP3 activity (e.g., by inhibiting binding of IGF to IGFR). In this method, one treats cells or cell membrane preparations comprising IGFR with detectably labeled IGF (e.g., radio-iodinated IGF) and detects binding of the detectable label. This method can employ, for example, CHO cells that include IGFR or cell membrane preparations therefrom. Ligand binding assays are well known in the art; see, for example, Steele-Perkins et al. (1988), *J. Biol. Chem.* 263: 11486–92.

We made the discoveries underlying the foregoing methods as follows.

Figure 1A:
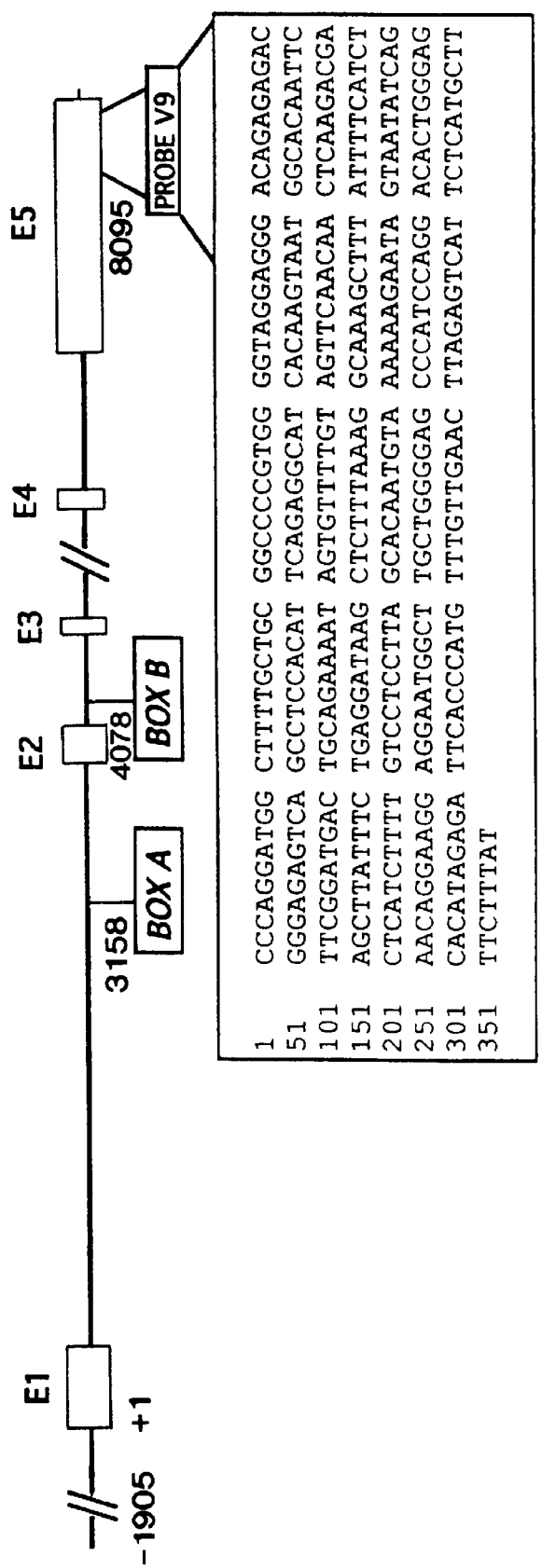
FIG. 1a–d shows the regulation of IGF-BP3 gene expression by wild type p53.
Figure 1B:
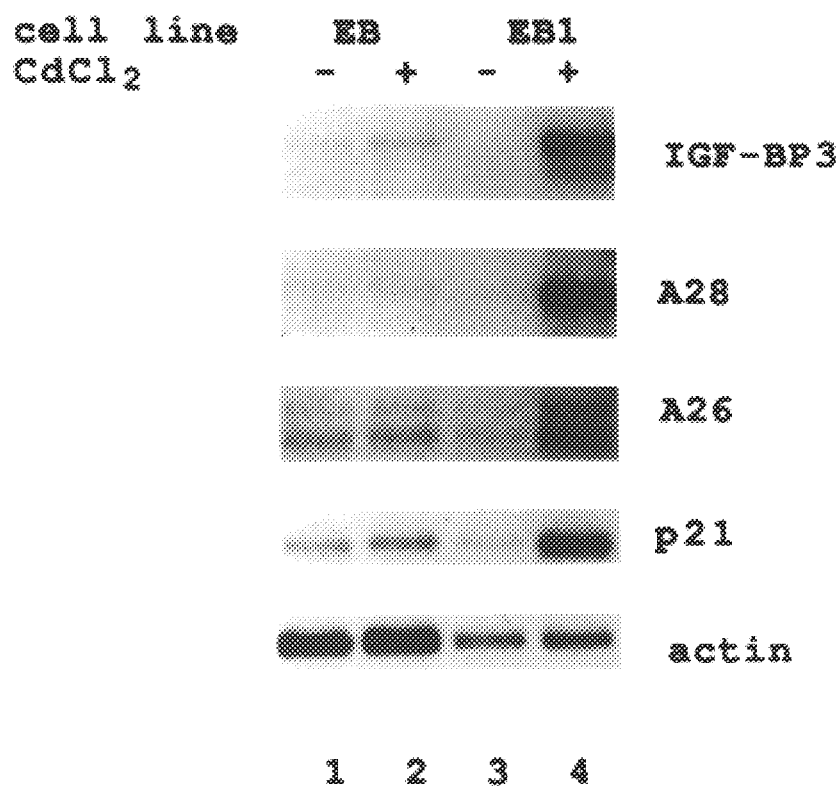
Figure 1C:
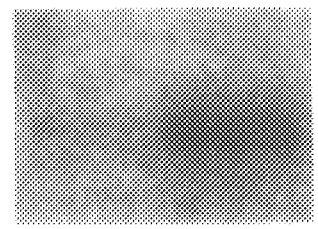
Figure 1C:
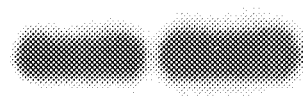

EB-1 colon carcinoma cells served as a model system to identify novel p53-induced target genes encoding potential mediators of p53 tumor suppression. These cells carry an inducible wild type p53 transgene under the control of the metallothionein promoter and undergo apoptosis upon induction of p53 by metal ions. Shaw et al. (1992), *Proc. Natl. Acad. Sci USA* 89: 4495–9. We used a subtractive cDNA cloning approach (see FIG. 1 and Materials and Methods), similar to the approach we used to identify novel p53-response genes in human Saos-2 osteosarcoma cells harboring a stably integrated and inducible temperature-sensitive p53-encoding transgene. Buckbinder et al. (1994), *Proc. Nati. Acad. Sci. USA* 91: 10640–4. This approach identified a number of enriched and non-overlapping cDNA fragments that derived from distinct p53-induced transcripts, as determined by Northern blot analysis. Nucleotide sequence analysis determined that one particular cDNA fragment was identical in sequence to a region in the insulin-like growth factor binding protein 3 gene, IGF-BP3. Cubbage et al. (1990), *J. Biol. Chem.* 265:12642–9; Genbank accession no. JO5537, JO5538. FIG. 1a shows schematically the structure of the IGF-BP3 gene reported in Cubbage et al. (1990), as well as the location and sequence of the isolated cDNA fragment (probe V9). This fragment maps to the 3' untranslated region within exon 5. FIG. 1b shows a northern blot analysis of $CdCl_2$-induced EB-1 cells using radiolabeled probe V9 to monitor IGF-BP3 mRNA expression. Induction of wt p53 is associated with a pronounced accumulation of IGF-BP3 mRNA levels 10 hours after addition of $CdCl_2$. This induction (about 14-fold) is comparable to that of other mRNAs encoded by previously characterized p53-response genes (p21, A28, and A26). See El-Deiry et al. (1993), *Cell* 75: 817–25; Buckbinder et al. (1994), *Proc. Natl. Acad. Sci. USA* 91: 10640–4 Notably, the induction is specific to clonal EB-1 cells expressing p53; we observed no induction in the parental EB cells. $CdCl_2$ treatment did not affect actin mRNA levels. FIG. 1c shows a northern blot analysis of IGF-BP3 mRNA expression in clonal Saos-2-D4H cells. These cells carry an inducible, temperature-sensitive transgene encoding mutant human p53V143A (described in detail in Buckbinder et al. (1994)). With tetracycline absent from the cell culture medium, the cells express high levels of p53V143A protein. As shown, shifting cells to the permissive temperature of 30° C. markedly induces IGF-BP3 mRNA expression. These findings confirm that wild type p53 specifically induces expression of an IGF-BP3 transcript in a different cell type, whereas mutant p53 does not induce IGF-BP3. Consistent with these findings, genotoxic stress (e.g., doxorubicin, ultraviolet light) induces expression of IGF-BP3 mRNA in normal diploid human fibroblasts (FIG. 4a).

Figure 1D:
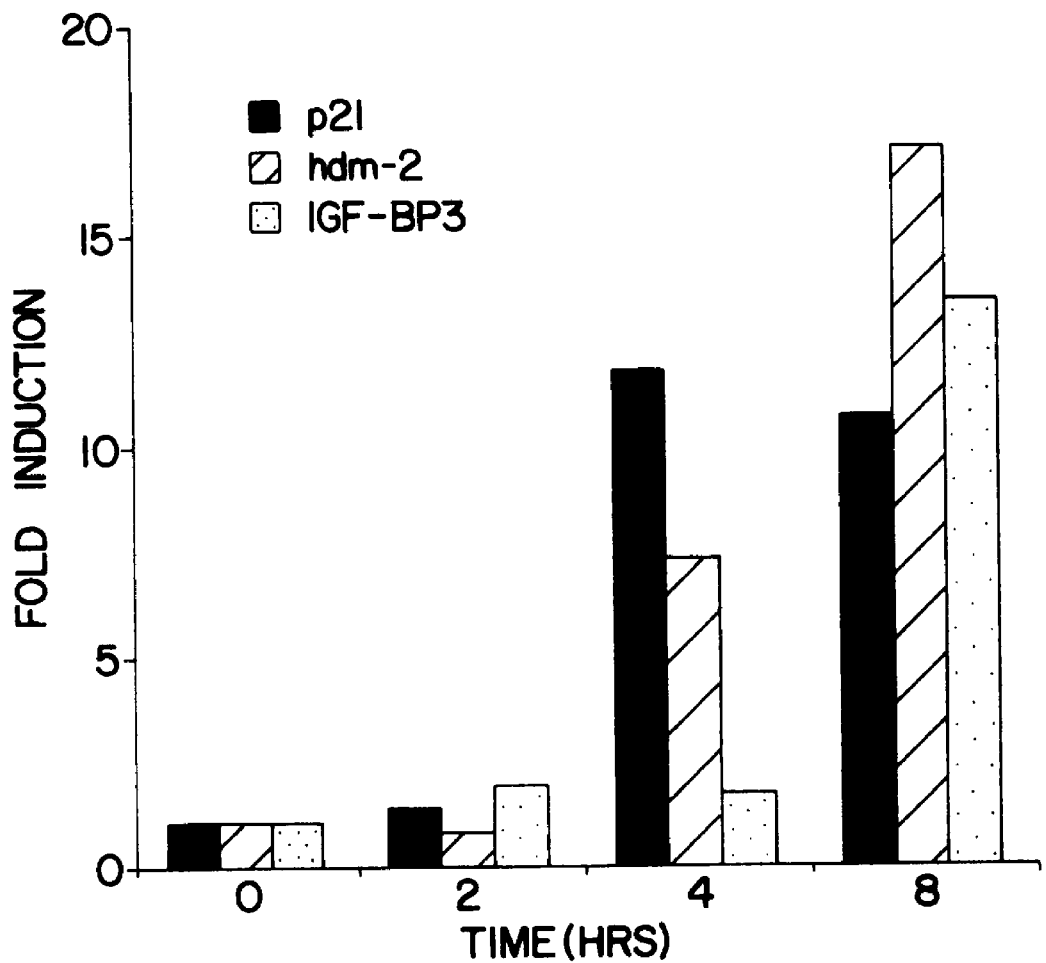
Figure 2B:
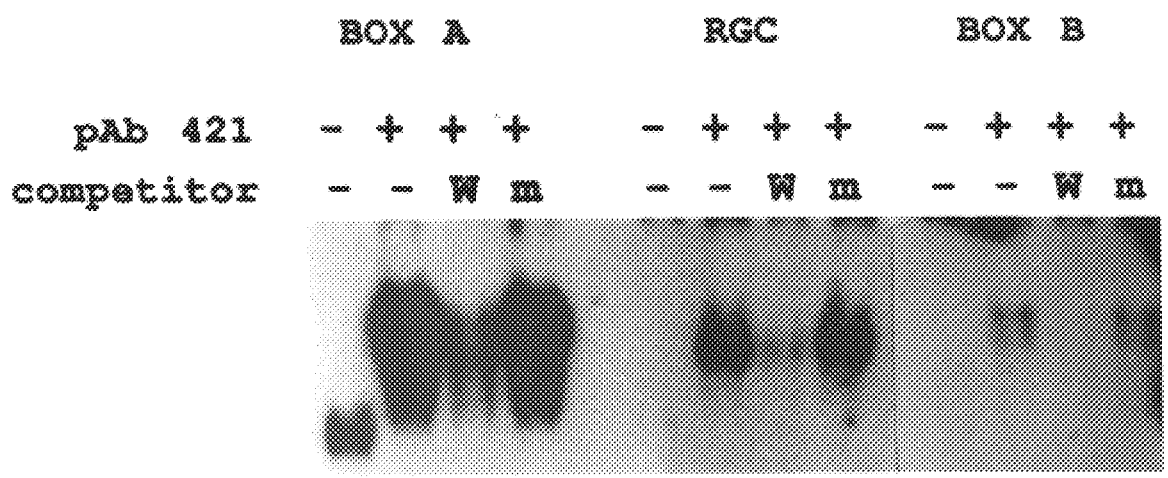
FIG. 2b shows specific binding of p53 to Box A and B DNA.
Figure 2C:
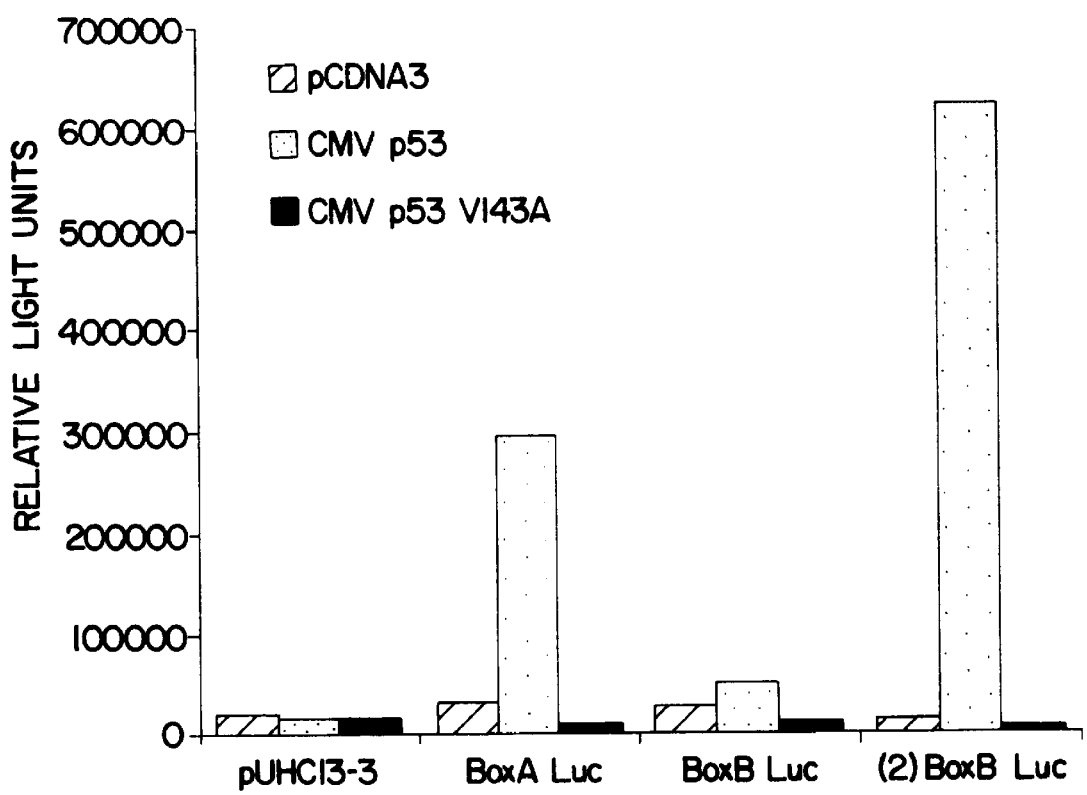
In FIG. 2c, Box A and B DNAs confer p53-inducibility to a heterologous promoter.
Figure 3A:
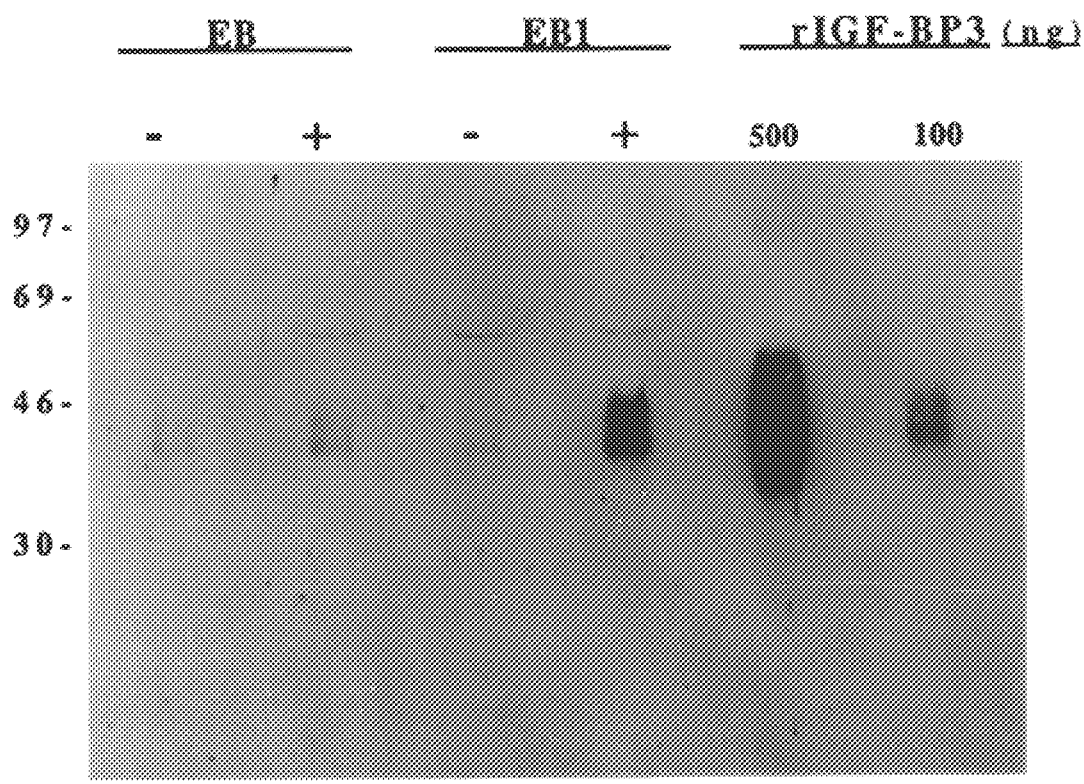
FIG. 3 shows inhibition of IGF-I induced DNA synthesis in Saos-2 cells by IGF-BP3. Part A shows secretion of IGF-BP3 by induced EB1 cells. Part B shows that Saos-2 cells are sensitive to mitogenic IGF-I activity. Part C shows that p53-induced IGF-BP3 secreted from EB1 cells inhibits IGF-I mitogenic activity.
Figure 3B:
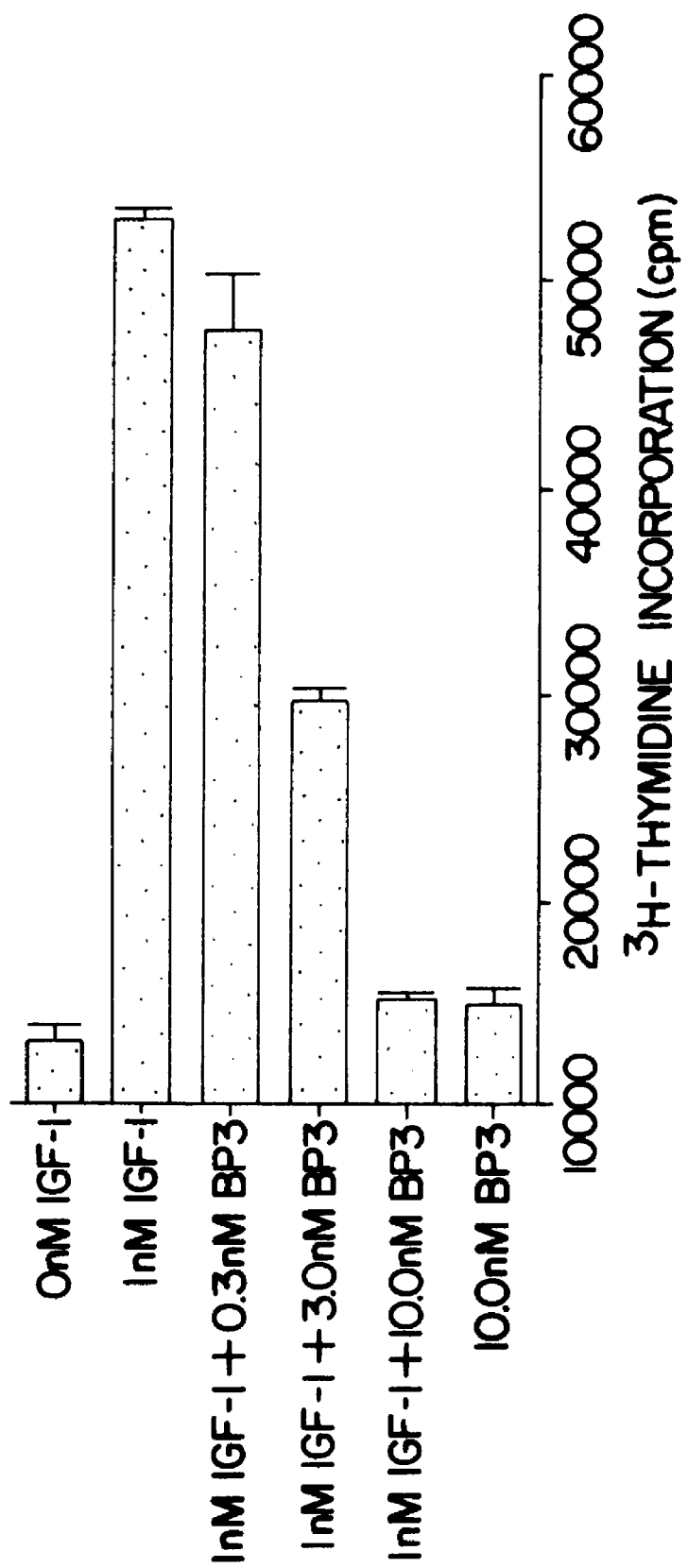
Figure 3C:
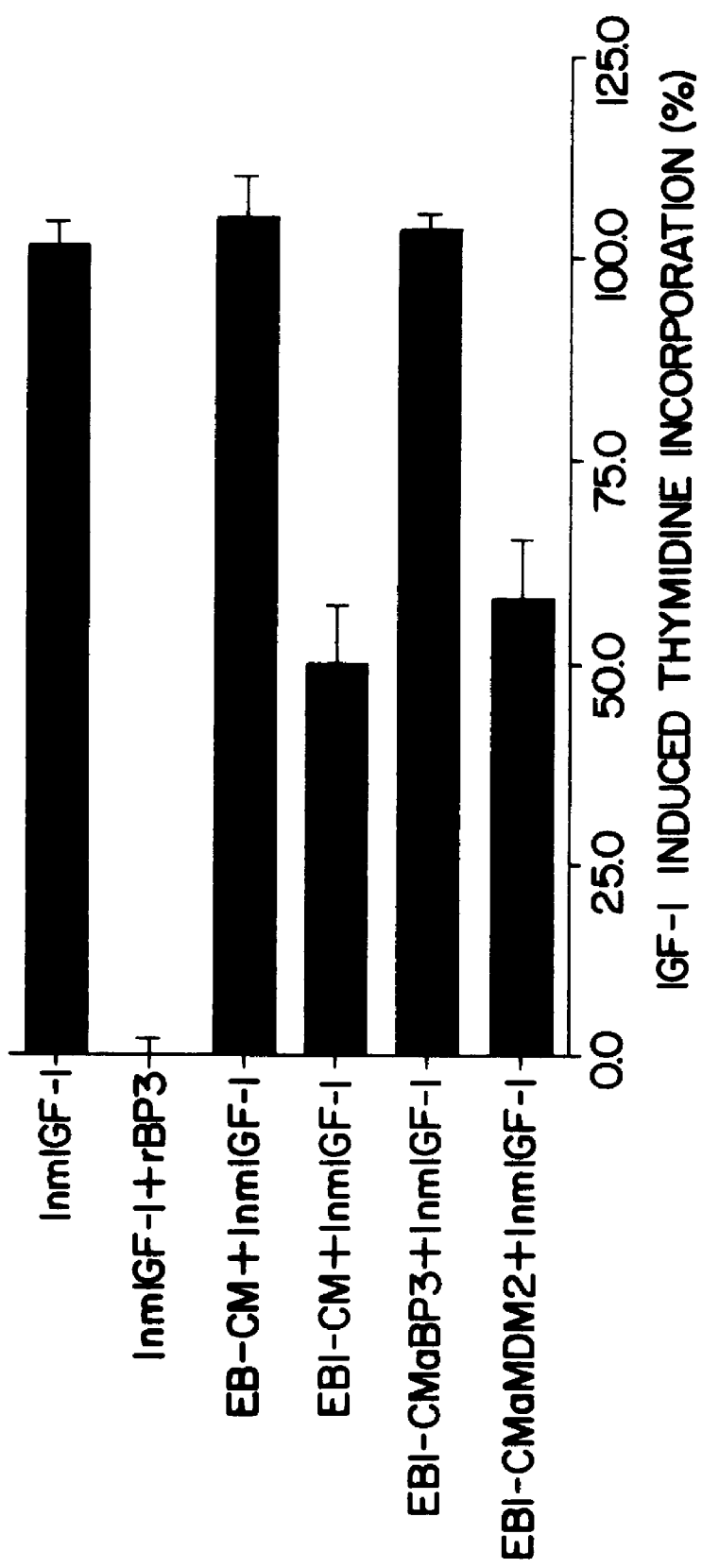

FIG. 1d shows a kinetic analysis of p53-mediated induction of IGF-BP3 mRNA expression in EB-1 cells. Compared to the increase in p21 and hdm-2 mRNA levels, induction of IGF-BP3 mRNA is somewhat delayed, increasing 4 to 8 hours after $CdCl_2$-stimulation. This raises the question whether the increase in IGF-BP3 gene expression represents a direct p53-response. We thus conducted a computer-based search for DNA sequences in the IGF-BP3 gene related to the p53 consensus binding site. El-Deiry et al. (1992), *Nature Genetics* 1: 45–9. This search revealed two potential p53 binding sites in the first (Box A) and second (Box B) introns of the IGF-BP3 gene, respectively (FIGS 1a and 2a). As shown in FIG. 2a, these binding sites are similar, but diverge in 2 or 3 nucleotides from the p53-consensus binding site. We also conducted DNA-binding and EMSA (Electro Mobility Shift Assay) analysis using purified baculovirus-produced human p53 protein. Takenaka et al. (1995), *J. Biol. Chem.* 270: 1–7. These analyses confirm that Box A and Box B are specific p53 binding sites (FIG. 2b). As shown in FIG. 2b for the RGC binding site, binding of wt p53 to Box A and Box B DNA sites is potentiated by addition of the C-terminal monoclonal antibody PAb421, which also produces the characteristic supershift in the EMSA. Other p53 binding sites had similar results. Kern et al. (1991), *Science* 252: 1708–11. Binding is specific, as indicated by the ability of a wild type but not mutant p53 consensus DNA sequence to compete for binding of p53 to either Box A or Box B DNAs. The weaker binding of p53 to Box B DNA, as compared to Box A DNA, is consistent with its weaker similarity to the p53 consensus binding sequence. FIG. 2c shows that both Box A and Box B DNA confer wild type specific p53-inducibility to a heterologous promoter when introduced into human Saos-2 cells, confirming the nature of these DNA sequences as p53-responsive elements. Consistent with the DNA binding studies, Box A confers considerably stronger induction by p53 than Box B. However, two copies of Box B DNA confer increased sensitivity to p53, indicating that Box B DNA, in cooperation with Box A DNA, could potentially contribute to a p53-dependent induction of IGF-BP3 gene transcription.

p53's induction of IGF-BP3 gene expression is significant because IGF-BP3 binds IGF-I and -II. Through such binding, IGF-BP3 reduces the availability of free IGFs and thus regulates their proliferative and mitogenic effects. (For reviews see Rechler (1993), *Vitamins and Hormones* 47: 1–114; Shimasaki. & Ling (1992), *Prog. Growth Factor Res.* 3: 243–66; Clemmons (1993), *Mol. Reprod. Dev.* 35:368–75; and Baserga (1994), *Cell* 79: 927–30). Consistent with this regulation, we found that p53-induced and recombinant IGF-BP3 inhibits IGF-I-induced DNA synthesis in Saos-2 osteosarcoma cells (FIGS. 3a, 3b, and 3c). These cells are the parental cells of the clonal -D4H cells, in which we found that p53 regulates IGF-BP3 expression (FIG. 1c). Addition of IGF-I (1 nM) to Saos-2 cells stimulates DNA synthesis, as indicated by an increase in $^3$H-thymidine incorporation. Concomitant addition of purified recombinant IGF-BP3 (0–10 nM) inhibits IGF-I induced DNA synthesis in a dose dependent manner. Addition of IGF-BP3 alone does not inhibit $^3$H-thymidine incorporation, indicating that IGF-BP3 specifically inhibits IGF-I-mediated DNA synthesis in these cells.

Both IGF-I and IGF-II act as autocrine and paracrine growth factors in adult tissues, affecting both normal and abnormal growth. Baserga (1994), *Cell* 79: 927–30; Goldring & Goldring (1991), *Eukar. Gene Express.* 1: 301–21; Baserga et al. (1994), *Adv. Exp. Med. Biol.* 343:105–12; Oh et al. (1993), *Growth Reg.* 3:113–23. The IGF-I/IGF-IR axis has been particularly well characterized. Loss of IGF-I and/or IGF-IR function is associated with:

cellular resistance to the mitogenic and transforming activities of the epidermal growth factor receptor;

resistance to the transforming activities of SV40 T antigen or SV40 T antigen and activated ras combined;

apoptosis in vivo;

loss of tumor cell growth in soft agar, syngeneic animals, and nude mice; and immunogenic responses that can apparently lead to even regression of established homologous tumors.

For reviews, see Baserga (1994), *Cell* 79: 927–30; and Baserga et al. (1994), *Adv. Exp. Med. Biol.* 343: 105–12. Recent reports suggest that IGF-I protects cells from c-myc-induced, p53-dependent apoptosis. Hermeking. & Eick (1994), *Science* 265: 2091–3; and Harrington et al. (1994), *EMBO J.* 13: 3286–95. Thus, IGF-I can act as a survival factor and may have a more accentuated role in oncogene-driven cells than in normal cells.

Consequently, we believe that IGF-BP3 plays an important autocrine and paracrine role in growth control by modulating IGFs-regulated processes. This role is especially significant because IGF-BP3 is expressed in multiple adult human tissues (FIG. 4a). Several experimental findings are consistent with this role for IGF-BP3:

IGF-BP3 inhibits IGF-I-induced DNA synthesis (FIG. 3).

Cells overexpressing IGF-BP3 are growth-inhibited. Cohen et al. (1993), *Mol. Endocrinol.* 7: 380–6.

IGF-BP3 expression is upregulated in quiescent and senescent cells (Moerman et al. (1993), *Exp. Geronotol.* 28: 361–70; and Grigoriev et al. (1994), *J. Cell. Physiol.* 160: 203–11).

IGF-BP3 expression is upregulated upon growth arrest of estradiol-dependent breast cancer cells. Pratt et al. (1993), *Cancer Res.* 53: 5193–8.

Furthermore, IGF-BP3 may regulate apoptosis by inhibiting IGF-I from acting as a survival factor. In this report, we show that IGF-BP3 links p53 to the IGF-I (II)/IGFR axis, providing insights into potential novel mechanisms whereby p53 may regulate cellular growth and apoptosis.

MATERIALS AND METHODS

Regulation of IGF-BP3 gene expression by wild p53 (FIG. 1). We treated parental EB and clonal EB-1 cells with or without $CdCl_2$ (6 μM) for 10 hours. We isolated poly(A)$^+$RNA and prepared Northern blots in quadruplicates. We hybridized the blots with cDNA probe V9 (IGF-BP3), with a cDNA probe for actin, and with cDNA probes for the p53-regulated transcripts p21/WAF1, A28 and A26, or actin, respectively, as previously described in Buckbinder et al. (1994), *Proc. Natl. Acad. Sci. USA* 91: 10640–4.

For FIG. 1b, we used the PCR-based cDNA library subtraction procedure described in Buckbinder et al. (1994) to identify transcripts induced by wt p53 in EB-1 cells activated by $CdCl_2$ (6 μM, 8 hours stimulation). Driver DNA consisted of cDNA prepared from $CdCl_2$ treated parental EB cells and untreated EB1 cells, as well as cloned cDNAs for p53, p21, and hdm-2 to allow for enrichment of novel regulated cDNA sequences. Buckbinder et al. (1994). We determined the nucleotide sequence for clone V9 by automated DNA sequence analysis (AB1 sequencer) and found it to be identical to a region (nucleotides 8095–8452) in the reported IGF-BP3 gene (Genbank accession number J05537). Buckbinder et al. (1994) describe the methods of RNA isolation and northern blot analysis that we used.

For FIG. 1c, we grew Saos-2-D4H cells at 37° C. without tetracycline to induce high levels of p53V143A protein expression. We subsequently incubated these cells for 7 hours at 37° or 30° C. (permissive temperature), as indicated. We prepared northern blots with equal amounts of poly(A)$^+$RNA and hybridized them sequentially with radiolabeled V9 or GAPDH cDNA probes.

Characterization of p53-binding and -responsive DNA elements in the IGF-BP3 gene (FIG. 2). We produced a His-p53 fusion protein in baculovirus, purified it, and conducted DNA binding reactions and EMSA analysis following the procedures described in Takenaka et al. (1995), *J. Biol. Chem.* 270: 1–7. We used double stranded DNA with following sequences. Box A (SEQ. ID. NO.: 2):

5'-TCGAGAAAACAAGCCACCAACATGCTTGC-3'
BOX B (SEQ. ID. NO.: 3):

5'-TCGAGAGGAGGGCAAGACCTGCCAAGCCT-GGGTA-3' consensus competitor (SEQ. ID. NO.: 5):

5'- GATCTACCCAGGCTTGGCAGGTCTTGCCCT-CCTC-3' mutant competitor (SEQ. ID. NO. 6):

5'- TCGAGCTTTGGACTTTTTCTGGCCA-3'.

We prepared luciferase reporter constructs by cloning Box A and B DNA into pUHC13-3 as described in Buckbinder et al. (1994). We confirmed the sequences by automated DNA sequencing. We co-transfected the p53 expression constructs pC53-SN3 and pC53-SCX3 (V143A), or control pcDNA3 vector (0.5 μg) with a luciferase reporter plasmid (1.5 μg) into 3×10$^5$ Saos-2 cells using lipofectamine (Gibco BRL). We determined luciferase activity as described in Buckbinder et al. (1994).

For FIG. 2a, we used EMSA to monitor binding of the purified baculovirus-produced p53 protein described in Takenaka et al. (1995). We performed binding reactions in the presence of monoclonal antibody PAb421 and wild type or mutant p53 consensus binding sites (200-fold molar excess), as indicated.

For FIG. 2c, we co-transfected luciferase reporter constructs with expression constructs encoding wt p53 or mutant p53V143A, or vector pcDNA, respectively. The luciferase constructs had either one copy of Box A, one or two copies of Box B, or multiple copies of the bacterial tet repressor binding site (pUHC13-3). We harvested the cells after 16 hours and assayed for luciferase activity.

Inhibition of IGF-I induced DNA synthesis in Saos-2 cells by IGF-BP3 (FIG. 3). Sub-confluent cultures of human Saos-2 osteosarcoma cells grew in enriched media (McCoy's media supplemented 15% fetal calf serum). We transferred these sub-confluent cultures to serum-free Hams F12 media (30 minutes) and then to F12 media supplemented with 0.1% bovine serum albumin (BSA, crystalline, Gibco BRL). These new cultures grew with or without recombinant IGF-I (1 nM, UBI) and with increasing amounts of recombinant IGF-BP3 (0–10 nM, UBI) or from conditioned media (CM) from treated EB or EB1 cells, as indicated. When conditioned media was used, it was dialyzed against Hams F12 media to remove CdCl2 and filter sterilized. In some cases conditioned media was depleted of IGF-BP3 by immuno-depletion using an IGF-BP3 monoclonal antibody (Accurate Scientific) or control MDM2 antibody (Oncogene Science). Following 18 hours of incubation, we pulsed the cells with $^3$H-thymidine (2 $\mu$Ci/mL) for 3 hours. We washed the cells in phosphate-buffered-saline (PBS, pH 7.4). We used liquid scintillation counting to measure $^3$H-thymidine incorporation into acid insoluble material. Average counts±S. D. from triplicate cultures are shown.

Multi-tissue expression of IGF-BP3 mRNA (FIG. 4). We used a northern blot with Poly(A)$^{+RNA}$ (2 $\mu$g/lane) from multiple adult human tissues (Clontech). We hybridized these blots with radiolabeled probe V9 (IGF-BP3).

What is claimed is:

1. A method of inhibiting growth of p53-related tumors, which comprises administering an effective amount of a modulator of IGF-BP3, wherein the modulator upregulates IGF-BP3 expression or activity.

2. The method of claim 1, wherein the modulator binds to SEQ. ID. NO.2 or 3 in the genomic DNA encoding IGF-BP3.

3. The method of claim 1, wherein the method further comprises administering a cytotoxic agent.

4. The method of claim 3, wherein the cytotoxic agent is selected from the group consisting of paclitaxel, cisplatin, doxorubicin, etoposide, camptothecin, mitomycin-C, cyclophosphamide, and methotrexate.

* * * * *